US011851393B2

(12) United States Patent
Early

(10) Patent No.: US 11,851,393 B2
(45) Date of Patent: *Dec. 26, 2023

(54) PROCESS FOR SYNTHESISING METHANOL

(71) Applicant: JOHNSON MATTHEY DAVY TECHNOLOGIES LIMITED, London (GB)

(72) Inventor: Simon Robert Early, London (GB)

(73) Assignee: Johnson Matthey Davy Technologies Limited, London (GB)

( * ) Notice: Subject to any disclaimer, the term of this patent is extended or adjusted under 35 U.S.C. 154(b) by 134 days.

This patent is subject to a terminal disclaimer.

(21) Appl. No.: 17/594,544

(22) PCT Filed: May 11, 2020

(86) PCT No.: PCT/GB2020/051142
§ 371 (c)(1),
(2) Date: Oct. 21, 2021

(87) PCT Pub. No.: WO2020/249924
PCT Pub. Date: Dec. 17, 2020

(65) Prior Publication Data
US 2022/0185753 A1 Jun. 16, 2022

(30) Foreign Application Priority Data
Jun. 12, 2019 (GB) ...................................... 1908449

(51) Int. Cl.
*C07C 29/151* (2006.01)
(52) U.S. Cl.
CPC ................................ *C07C 29/1518* (2013.01)

(58) Field of Classification Search
CPC ..... C07C 29/1518; C07C 31/04; C01B 3/382; C01B 2203/0233; C01B 2203/0244;
(Continued)

(56) References Cited

U.S. PATENT DOCUMENTS 4,321,234 A 3/1982 Ohsaki et al.
4,411,877 A 10/1983 Notman
(Continued)

FOREIGN PATENT DOCUMENTS

EP 1412312 A1 4/2004
EP 2228358 A1 9/2010
(Continued)

*Primary Examiner* — Jafar F Parsa
(74) *Attorney, Agent, or Firm* — BakerHostetler

(57) ABSTRACT

A process for synthesising methanol is described comprising the steps of (i) forming a synthesis gas containing hydrogen, carbon monoxide and carbon dioxide from a hydrocarbon feedstock in a reforming unit comprising a heat exchange reformer and autothermal reformer in series; (ii) cooling the synthesis gas in the heat exchange reformer and one or more further stages of heat exchange, and recovering process condensate from the cooled synthesis gas to form a make-up gas; (iii) passing a feed gas comprising the make-up gas to a methanol synthesis loop comprising one or more methanol synthesis reactors; (iv) recovering a product gas mixture containing methanol from the methanol synthesis loop, and separating the crude methanol from an unreacted gas mixture; and (v) recycling a portion of the unreacted gas mixture to the methanol synthesis loop and recovering a portion of the unreacted gas mixture as a purge gas stream.

16 Claims, 1 Drawing Sheet

(58) Field of Classification Search
CPC .... C01B 2203/0255; C01B 2203/0261; C01B 2203/062
See application file for complete search history.

(56) References Cited

U.S. PATENT DOCUMENTS

| | | |
|---|---|---|
| 4,788,175 A | 11/1988 | Short et al. |
| 5,827,901 A | 10/1998 | Konig et al. |
| 6,191,174 B1 | 2/2001 | Early et al. |
| 6,218,439 B1 | 4/2001 | Kobayashi et al. |
| 7,790,775 B2 | 9/2010 | Early |
| 8,785,506 B2 | 7/2014 | Gamlin |
| 2009/0105356 A1 | 4/2009 | Bormann et al. |
| 2009/0123348 A1 | 5/2009 | Brady et al. |
| 2009/0184293 A1 | 7/2009 | Han |
| 2011/0160313 A1 | 6/2011 | Ji |
| 2018/0305281 A1* | 10/2018 | Dahl ........................ B01L 3/06 |

FOREIGN PATENT DOCUMENTS

| | | |
|---|---|---|
| GB | 1578270 A | 11/1980 |
| WO | 97/05947 A1 | 2/1997 |
| WO | 2005/070855 A1 | 8/2005 |
| WO | 2006/126017 A1 | 11/2006 |
| WO | 2009/105356 A1 | 8/2009 |
| WO | 2011/088981 A1 | 7/2011 |
| WO | 2016/180812 A1 | 11/2016 |
| WO | 2017/121980 A1 | 7/2017 |
| WO | 2017/121981 A1 | 7/2017 |
| WO | 2019/008315 A1 | 1/2019 |
| WO | 2019/008317 A1 | 1/2019 |

* cited by examiner

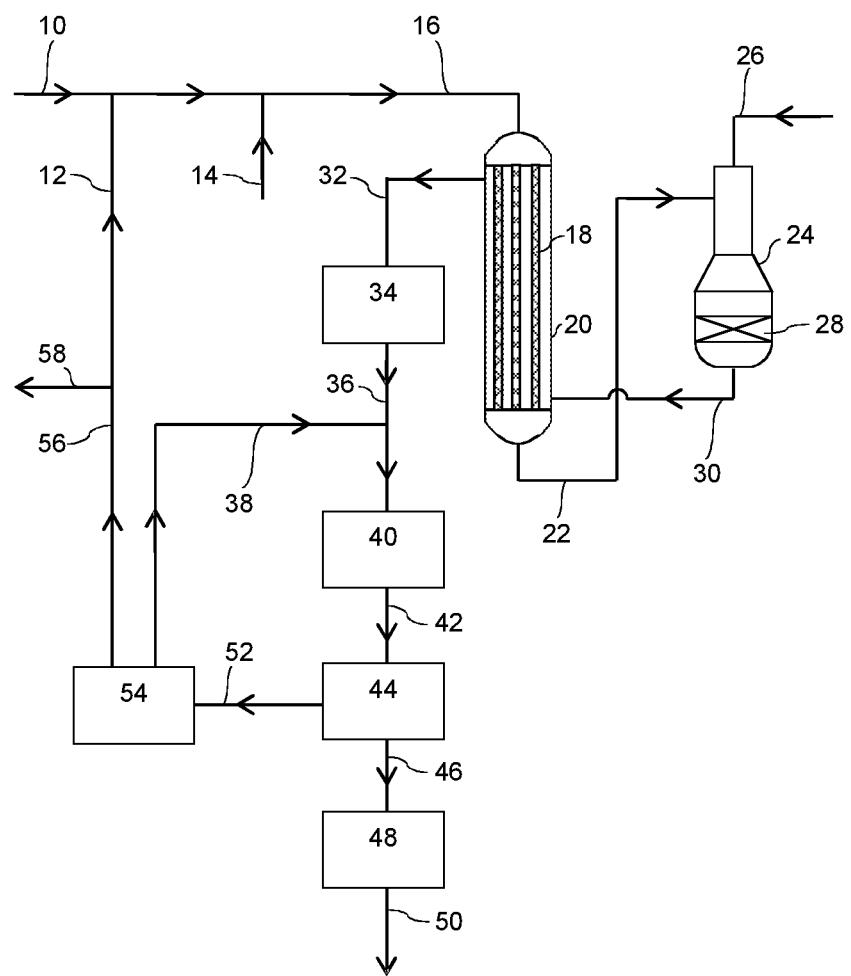

PROCESS FOR SYNTHESISING METHANOL

This invention relates to a process for synthesising methanol.

Methanol synthesis is generally performed by passing a synthesis gas comprising hydrogen and carbon monoxide and/or carbon dioxide at an elevated temperature and pressure through one or more beds of a methanol synthesis catalyst, which is often a copper-containing composition, in a synthesis reactor. A crude methanol is generally recovered by cooling the product gas stream to below the dew point and separating off the product as a liquid. The crude methanol is typically purified by distillation. The process is often operated in a loop: thus unreacted gas may be recycled to the synthesis reactor as part of the feed gas via a circulator. Fresh synthesis gas, termed make-up gas, is added to the recycled unreacted gas to form the feed gas stream. A purge stream is often taken from the circulating gas stream to avoid the build-up of inert gasses in the loop.

Methanol synthesis may be described by the following two equations:

$$3H_2 + CO_2 \rightleftharpoons CH_3OH + H_2O$$

$$2H_2 + CO \rightleftharpoons CH_3OH$$

There are two stoichiometric values that are commonly used to describe the proportions of the reactants fed to the methanol synthesis reactor. These are R and Z and may be determined from the molar concentrations of the components in the synthesis gas as follows;

$$R = ([H_2] - [CO_2])/([CO] + [CO_2])$$

$$Z = [H_2]/(2[CO] + 3[CO_2])$$

In addition, for methanol synthesis, it is often useful to determine a value S; being the sum of the Nm³/h of $H_2$+Nm³/h of CO in the synthesis gas. S, Z and R may then be linked by the equation:

Maximum methanol make (Nm³/h)=$Z \cdot S/(R+1)$ for $Z \leq 1$

Maximum methanol make (Nm³/h)=$S/(R+1)$ for $Z > 1$

The ideal stoichiometric mixture arises when there is enough hydrogen to convert all of the carbon oxides into methanol. This is when R=2 and Z=1. However different synthesis gas generation techniques produce different synthesis gases having different proportions of the reactants.

The synthesis gas is typically generated using a fired steam reformer that reforms a mixture of a hydrocarbon feedstock, such as natural gas, and steam. In such plants nearly 30% of the natural gas is used for fuel purposes and the other 70% as feedstock. The combustion of the fuel generates considerable carbon dioxide emissions from the process.

U.S. Pat. No. 6,191,174 discloses a process for the production of methanol from a hydrocarbon feedstock comprising: contacting a vaporous mixture comprising the feedstock and steam in a steam reforming zone with a catalyst effective for catalysis of at least one reforming reaction; recovering from the reforming zone a synthesis gas mixture comprising carbon oxides, hydrogen and methane; supplying material of the synthesis gas mixture to a methanol synthesis zone charged with a methanol synthesis catalyst and maintained under methanol synthesis conditions; recovering from the methanol synthesis zone a product gas mixture comprising methanol and unreacted material of the synthesis gas mixture; supplying material of the product gas mixture to a methanol recovery zone maintained under methanol recovery conditions; recovering from the methanol recovery zone a crude methanol product stream and a vaporous steam comprising unreacted material of the synthesis gas mixture; separating material of the synthesis gas mixture into a first hydrogen-rich stream and a second carbon oxides-rich stream comprising carbon oxides and methane; supplying at least part of the first hydrogen-rich stream to the steam reforming zone as fuel; and recycling at least part of the second carbon oxides-rich stream to the steam reforming zone to form part of the mixture of the vaporous mixture comprising the feedstock and steam. The steam reforming zone comprises a compact fired reformer.

As is evident in this disclosure, a methanol plant also typically includes several large compressors, traditionally driven by steam generated by heat recovered from the process and supplemented by steam from one or more fired boilers and heaters.

The Applicants have realised that where the synthesis gas is generated by a combination of a heat exchange reformer and autothermal reformer in series, the process does not need to raise steam for-power. While there is still a need for the synthesis gas generation, the fuel value of the loop purge gas is more than sufficient for this process. Thus, the fuel value of a carbon rich gas recovered from the purge gas in a heat exchange reformer-autothermal former flowsheet can exceed the fuel requirements of fired heaters and boilers on the plant, particularly when electric motors are used to drive the compressors. By eliminating the need for steam-to-power, the process overall uses less hydrocarbon as fuel thereby reducing its carbon dioxide emissions compared to an equivalent fired reformer flowsheet.

Accordingly the invention provides a process for synthesising methanol comprising the steps of (i) forming a synthesis gas containing hydrogen, carbon monoxide and carbon dioxide from a hydrocarbon feedstock in a reforming unit comprising a heat exchange reformer and autothermal reformer in series; (ii) cooling the synthesis gas in the heat exchange reformer and one or more further stages of heat exchange, and recovering process condensate from the cooled synthesis gas to form a make-up gas; (iii) passing a feed gas comprising the make-up gas to a methanol synthesis loop comprising one or more methanol synthesis reactors; (iv) recovering a product gas mixture containing methanol from the methanol synthesis loop, cooling the product gas mixture to below the dew point to condense crude methanol, and separating the crude methanol from an unreacted gas mixture; and (v) recycling a portion of the unreacted gas mixture to the methanol synthesis loop and recovering a portion of the unreacted gas mixture as a purge gas stream, wherein a hydrogen-rich stream and a carbon-rich stream are separated from the purge gas, a portion of the hydrogen-rich stream is fed to the methanol synthesis loop and a portion of the carbon-rich stream is fed to the reformer unit.

By "carbon-rich stream" we mean a gas stream that has a higher proportion of carbon-containing compounds (carbon monoxide, carbon dioxide and methane) than the purge gas. While individual components may have the same, or even lower, proportion than in the purge gas, the total of all carbon-containing compounds will be higher in the carbon-rich stream.

Methane is inert in the methanol synthesis reactions but is a valuable feedstock for the reforming process used to make the synthesis gas and the carbon-rich stream is useful as either fuel or as feedstock.

In the process of the invention the hydrocarbon feedstock may be any gaseous or low boiling hydrocarbon feedstock such as natural gas, associated gas, LPG, petroleum distillate or naphtha. It is preferably methane, associated gas or natural gas containing a substantial proportion, e.g. over 85% v/v methane. Natural gas is an especially preferred feedstock. The feedstock is typically compressed to a pressure in the range 10-100 bar abs.

If the hydrocarbon feedstock contains sulphur compounds, before or after compression, the feedstock is preferably subjected to desulphurisation, e.g. hydrodesulphurisation using Co or Ni catalysts and absorption of hydrogen sulphide using a suitable absorbent, e.g. a zinc oxide bed. To facilitate this and/or reduce the risk of carbon laydown in the reforming process, hydrogen is preferably added to the hydrocarbon feedstock. The amount of hydrogen in the resulting mixed gas stream may be in the range 1-20% vol, but is preferably in the range 1-10%, more preferably in the range 1-5%. In a preferred embodiment a portion of the hydrogen-rich stream is mixed with the hydrocarbon feed stream. The hydrogen stream may be combined with the hydrocarbon upstream and/or downstream of any hydrodesulphurisation stage.

In steam reforming, the hydrocarbon feedstock is mixed with steam: this steam introduction may be effected by direct injection of steam and/or by saturation of the feedstock by contact of the latter with a stream of heated water in a saturator. One or more saturators may be used. If desired, a portion of the hydrocarbon stream may bypass the steam addition, e.g. the saturator. The amount of steam introduced may be such as to give a steam to carbon ratio of 1 to 3, preferably 1 to 2, i.e. 1 to 2 moles of steam per gram atom of hydrocarbon carbon in the feedstock. The amount of steam is preferably minimised as this leads to a lower cost, more efficient process.

The hydrocarbon/steam mixture is then desirably preheated prior to reforming. This may be achieved by the use of a feed-effluent heat exchanger, with the mixture being heated by the partially cooled reformed gas mixture. Desirably, the mixed stream is heated to 400-500° C.

The carbon-rich stream is also fed to the reforming unit. This may be conveniently achieved by combining the hydrocarbon or hydrocarbon and steam mixture with the carbon-rich stream using any known method. Less-preferably, the carbon-rich stream may be combined with a reformed gas mixture fed to the autothermal reformer.

The resultant feedstock/steam mixture is then subjected to reforming in a reforming unit in two stages in series, which may be termed primary steam reforming and secondary or autothermal reforming. The first stage or primary reforming is effected using a heat exchange reformer, also termed a gas-heated reformer (GHR). In a preferred type of heat exchange reformer, the catalyst is disposed in tubes extending between a pair of tube sheets through a heat exchange zone. Reactants are fed to a zone above the upper tube sheet and pass through the tubes and into a zone beneath the lower tube sheet. The heating medium is passed through the zone between the two tube sheets. Heat exchange reformers of this type are described in GB1578270, WO97/05947 and US2009/0123348.

The compressed, heated feedstock/steam mixture is passed through the catalyst-filled tubes in the heat exchange reformer. During passage through the reforming catalyst, the endothermic reforming reaction takes place with the heat required for the reaction being supplied from the second stage or secondary reformed gas flowing past the exterior surface of the tubes. The primary reforming catalyst used in the heat exchange reformer is usually nickel supported on a refractory support such as rings or multi-holed pellets of calcium aluminate cement, alumina, titania, zirconia and the like. Alternatively, a combination of a nickel and precious metal catalyst may be used. For example, a portion of the nickel catalyst may be replaced with a precious metal catalyst, such as a ruthenium-based catalyst. Alternatively, or additionally, a structured steam reforming catalyst in which a wash coat of steam reforming catalyst on a structured, e.g. monolithic, ceramic or metal support may be used.

The temperature of the secondary reformed gas is preferably sufficient that the gas undergoing primary reforming leaves the primary reformer at a temperature in the range 650-850° C., preferably 720-780° C.

The primary reformed gas produced by the heat exchange reformer, which comprises methane, hydrogen, steam and carbon oxides, is fed, preferably without any dilution or heat exchange, to an autothermal or secondary reformer in which it is subjected to the second stage or secondary reforming.

The autothermal reformer will generally comprise a burner disposed near the top of the reformer to which is fed the primary reformed gas and an oxygen-containing gas, a combustion zone beneath the burner through which, typically, a flame extends, above a fixed bed of particulate steam reforming catalyst. In autothermal or secondary reforming, the heat for the endothermic steam reforming reactions is provided by combustion of hydrocarbon and hydrogen in the feed gas. The primary reformed gas is typically fed to the top of the reformer and the oxygen-containing gas fed to the burner, mixing and combustion occur downstream of the burner generating a heated gas mixture which is brought to equilibrium as it passes through the steam reforming catalyst. Whereas some steam may be added to the oxygen containing gas, preferably no steam is added so that the low overall steam ratio for the reforming process is achieved. The secondary reforming catalyst is usually nickel supported on a refractory support such as rings or pellets of calcium aluminate cement, alumina, titania, zirconia and the like. In a preferred embodiment, the secondary reforming catalyst comprises a layer of a higher activity Ni and/or Rh on zirconia catalyst over a conventional Ni on alumina catalyst to reduce catalyst support volatilisation.

The oxygen-containing gas preferably comprises ≥95% vol. $O_2$, which may be provided by an air separation unit (ASU) or from another oxygen source.

The amount of oxygen-containing gas required in the secondary reformer is determined by two main considerations, viz. the desired composition of the product gas, and the heat balance of the heat exchange reformer. In general, increasing the amount of oxygen, thereby increasing the temperature of the reformed gas leaving the secondary reformer, causes the $[H_2]/[CO]$ ratio to decrease and the proportion of carbon dioxide to decrease. Alternatively, if the conditions are arranged such that the product composition and temperature is kept constant, increasing the temperature at which the feedstock is fed to the heat exchange reformer decreases the amount of oxygen required (at a constant oxygen feed temperature).

The amount of oxygen-containing gas added is preferably such that 40 to 60 moles of oxygen are added per 100 gram atoms of hydrocarbon in the feed to the primary reforming stage. Preferably the amount of oxygen added is such that the secondary reformed gas leaves the secondary reformer at a temperature in the range 800-1050° C., more preferably 900-1000° C.

The secondary reformed gas is then used to provide the heat required for the primary reforming step by using the secondary reformed gas as the hot gas flowing past the tubes of the heat exchange reformer. During this heat exchange the secondary reformed gas cools by transferring heat to the gas undergoing primary reforming. Preferably the secondary reformed gas cools by several hundred degrees Centigrade but of course it will leave the heat exchange reformer at a temperature somewhat above the temperature at which the feedstock/steam mixture is fed to the catalyst-filled tubes in the heat exchange reformer. Preferably the secondary reformed gas leaves the heat exchange reformer at a temperature in the range 500-650° C.

After leaving the heat exchange reformer, the secondary reformed gas is then further cooled in one or more steps of heat exchange. Heat recovered during this cooling may be employed for reactants pre-heating and/or for heating water used to provide the steam employed in the primary reforming step. In a preferred embodiment, the secondary reformed gas mixture exiting the shell side of the heat exchange reformer is used to preheat the feedstock/steam mixture fed to the tubes in the heat exchange reformer.

The cooling is performed to lower the temperature of the synthesis gas from the autothermal or secondary reformer to below the dew point such that steam present in the synthesis gas condenses. The liquid process condensate may be separated from the synthesis gas, which may be termed make-up gas at this point, by conventional gas-liquid separation equipment.

The make-up gas comprises hydrogen, carbon monoxide, carbon dioxide, and small amounts of unreacted methane, argon and nitrogen. The composition of make-up gas is preferably; 10-20 mol % carbon monoxide, 0.5-15 mol % carbon dioxide, 55-85% hydrogen and the balance one or more inert gases, including methane. The R value of the make-up gas (before hydrogen-rich gas is added) is preferably 1.95-2.05 and Z is preferably 0.95-1.05.

The make-up gas may be compressed in a synthesis gas compressor to the desired methanol synthesis pressure before feeding the make-up gas, mixed with the hydrogen rich gas, to the methanol synthesis loop. Preferably the synthesis gas compressor is electrically driven.

Any methanol synthesis loop may be used in the process of the present invention. The methanol synthesis loop comprises one or more methanol synthesis reactors, for example, first, second and optionally third methanol synthesis reactors, each containing a bed of methanol synthesis catalyst, arranged in series and/or parallel that each produce product gas streams containing methanol. The methanol synthesis loop may therefore comprise one, two or more methanol synthesis reactors each containing a bed of methanol synthesis catalyst, and each fed with a feed gas comprising hydrogen and carbon dioxide, each producing a gas mixture containing methanol. A product gas mixture containing methanol is recovered from at least one methanol synthesis reactor. Methanol is recovered from one or more of the product gas mixtures. This may be achieved by cooling one or more of the methanol product gas streams to below the dew point, condensing methanol, and separating a crude liquid methanol product from the unreacted gases.

Conventional heat exchange and gas-liquid separation equipment may be used. A particularly suitable heat exchange apparatus includes a gas-gas interchanger that uses a feed gas mixture for a methanol synthesis reactor to cool a methanol product gas stream from that reactor. The methanol product gas streams may be treated separately or may be combined before cooling and/or separating the crude liquid methanol product.

Separation of the crude liquid methanol product from one or more of the methanol product gas streams produces an unreacted gas mixture. A portion of the unreacted gas mixture is returned as a recycle or loop gas stream to one or more of the methanol synthesis reactors. Unreacted gas separated from a product gas mixture recovered from one methanol synthesis reactor may be returned to the same or a different methanol synthesis reactor. The unreacted gas mixture comprises hydrogen, carbon monoxide, and carbon dioxide and so may be used to generate additional methanol. The recycle gas stream may be recovered from at least one of one of the methanol product gas streams and recycled to at least one of the methanol synthesis reactors. If there is more than one recycle gas stream, these may be recycled separately to one or more of the methanol synthesis reactors or combined and fed to one or more of the methanol synthesis reactors.

The methanol synthesis reactor in the methanol synthesis loop may be an un-cooled adiabatic reactor. Alternatively, the methanol synthesis reactor may be cooled by heat exchange with a synthesis gas, such as in a quench reactor, or a reactor selected from a tube-cooled converter or a gas-cooled converter. Alternatively, the methanol synthesis reactor may be cooled by boiling water under pressure, such as in an axial-flow steam-raising converter, or a radial-flow steam-raising converter.

In an adiabatic reactor, the synthesis gas may pass axially, radially or axially and radially through a fixed bed of particulate methanol synthesis catalyst. The exothermic methanol synthesis reactions occur resulting in an increase in the temperature of the reacting gases. The inlet temperature to the bed therefore is desirably cooler than in cooled reactor systems to avoid over-heating of the catalyst which can be detrimental to selectivity and catalyst life. Alternatively, a cooled reactor may be used in which heat exchange with a coolant within the reactor may be used to minimise or control the temperature rise. A number of cooled reactor types exist that may be used. In one configuration, a fixed bed of particulate catalyst is cooled by tubes or plates through which a coolant heat exchange medium passes. In another configuration, the catalyst is disposed in tubes around which the coolant heat exchange medium passes. The methanol synthesis reactors may be cooled by the feed gas or by boiling water, typically under pressure. For example, the methanol synthesis reactor may be an axial steam raising converter, a radial-flow steam raising converter, a gas-cooled converter or a tube cooled converter.

In an axial-flow, steam-raising converter (aSRC), the synthesis gas typically passes axially through vertical, catalyst-containing tubes that are cooled in heat exchange with boiling water under pressure flowing outside the tubes. The catalyst may be provided in pelleted form directly in the tubes or may be provided in one or more cylindrical containers that direct the flow of synthesis gas both radially and axially to enhance heat transfer. Such contained catalysts and their use in methanol synthesis are described in U.S. Pat. No. 8,785,506. Steam raising converters in which the catalyst is present in tubes cooled by boiling water under pressure offer a particularly useful means to remove heat from the catalyst.

In a radial-flow steam raising converter (rSRC) the synthesis gas typically passes radially (inwards or outwards) through a bed of particulate catalyst which is cooled by a plurality of tubes or plates through which boiling water under pressure is fed as coolant. Such reactors are known and are described for example in U.S. Pat. No. 4,321,234. They offer a lower pressure drop than an aSRC but have a more complicated internal construction.

In a tube-cooled converter, the catalyst bed is cooled by synthesis gas passing through tubes disposed within the bed that are open-ended and discharge the heated gas to the space above the catalyst within the reactor shell. The heated gas may then pass directly through the bed of catalyst without leaving the converter. TCC's can provide sufficient cooling area for a range of synthesis gas compositions and may be used under a wide range of conditions. As an alternative to a TCC, a gas-cooled converter (GCC) may be used to cool the catalyst bed by passing the synthesis gas though tubes or plates in a heat exchanger-type arrangement. In this case the heated synthesis gas is withdrawn from the converter before being returned back to the catalyst bed. An example of a GCC is described in U.S. Pat. No. 5,827,901.

Alternatively, the methanol synthesis reactor may be a quench reactor in which one or more fixed beds of particulate methanol synthesis catalyst are cooled by a synthesis gas mixture injected into the reactor within or between the beds. Such reactors are described, for example, in U.S. Pat. No. 4,411,877.

In a process comprising first and second methanol synthesis reactors, the first methanol synthesis reactor is preferably cooled by boiling water, such as in an axial-flow steam-raising converter or a radial-flow steam-raising converter, more preferably an axial-flow steam raising converter. The second methanol synthesis reactor may be a radial-flow steam-raising converter. Such arrangements are particularly useful in the present invention due to the characteristics and performance of these reactors with different feed gas mixtures. Alternatively, the second methanol may be cooled by a synthesis gas, e.g. a gas comprising hydrogen and carbon dioxide. Accordingly, the second methanol synthesis reactor may be a cooled reactor selected from a tube cooled converter (TCC) and a gas-cooled converter (GCC). A tube-cooled converter is preferred because of its simpler design. If a third methanol synthesis reactor is present, it is preferably cooled by boiling water. The third methanol synthesis reactor may then suitably be a steam-raising converter selected from an axial-flow steam-raising converter and a radial-flow steam-raising converter, most preferably an axial-flow steam raising converter. The first and second methanol synthesis reactors may be connected in series in which case the synthesis gas fed to the second methanol synthesis reactor comprises at least a portion of a methanol product gas stream recovered from the first methanol synthesis reactor. In such an arrangement, preferably the synthesis gas fed to the second methanol synthesis reactor comprises all of the methanol product gas stream recovered from the first methanol synthesis reactor. Particularly preferred methanol loops are described in U.S. Pat. No. 7,790,775, WO2017/121980 and WO2017/121981.

The methanol synthesis catalysts in each of the methanol synthesis reactors may be the same or different. The methanol synthesis catalysts are preferably copper-containing methanol synthesis catalysts, which are commercially available. In particular, the methanol synthesis catalysts are one or more particulate copper/zinc oxide/alumina catalysts, which may comprise one or more promoters. Particularly suitable catalysts are Mg-promoted copper/zinc oxide/alumina catalysts as described in U.S. Pat. No. 4,788,175.

Methanol synthesis may be effected in the one or more methanol synthesis reactors at pressures in the range 10 to 120 bar abs, and temperatures in the range 130° C. to 350° C. The pressures at the one or more reactor inlets is preferably 50-100 bar abs, more preferably 70-90 bar abs. The temperature of the synthesis gas at the one or more reactor inlets is preferably in the range 200-250° C. and at the one or more reactor outlets preferably in the range 230-280° C.

The portion of the unreacted gas mixture making up the recycle gas stream to the methanol synthesis loop will typically be at a lower pressure than the make-up gas and so preferably the recycle gas stream is compressed by one or more compressors or circulators. At least one compressor is used to circulate the unreacted gas stream. Preferably the circulating compressor is electrically driven. The resulting compressed recycle gas stream may be mixed with make-up gas and the hydrogen-rich stream to form the feed to the one or more methanol synthesis reactors in the methanol synthesis loop.

The recycle ratios to form the feed gas mixtures to the one or more methanol synthesis reactors may be in the range 0.5:1 to 5:1 preferably 1:1 to 3:1. By the term "recycle ratio", we mean the molar flow ratio of the recycled unreacted gas stream to the make-up gas that form the gas mixtures fed to the one or more methanol synthesis reactors.

It will be understood that by adding the hydrogen-rich gas stream to the make-up gas, that the stoichiometry value R will be increased, preferably to a value greater than 2. An R value greater than 2 indicates that there is a stoichiometric excess of hydrogen, and the high conversion of carbon oxides into methanol in a modern synthesis loop will cause the R value at the inlet of the methanol synthesis reactors to be in the range of 3 to 5, or even higher. The addition of a hydrogen-rich gas that has been recovered from the loop purge gas means that the methanol synthesis reactors can be operated at their optimum R value of 3 to 5 with a make-up gas with an R value close to the stoichiometric optimum value of 2 that will maximise the methanol production.

A portion of the unreacted gas mixture separated from the crude liquid methanol is removed from the loop as the purge gas stream. The purge gas stream may be removed continuously or periodically to prevent the unwanted build-up of inert gases, such as nitrogen, argon and methane in the synthesis loop. The purge gas stream may be recovered from the separated unreacted gases before or after compression in the circulator. Purge gas streams, especially in processes using steam reforming as a source of the make-up gas, are hydrogen rich. The purge stream preferably contains 50-90% by volume of hydrogen and one or more of carbon monoxide, carbon dioxide, nitrogen, argon and methane.

In the present invention, at least a portion of the purge gas stream is separated into a hydrogen-rich gas stream and a carbon-rich gas stream. Preferably all of the purge gas stream is subjected to the separation step. A portion of the hydrogen-rich stream is fed to the methanol synthesis loop and a portion of the carbon-rich stream is fed to the reformer unit. The separation of the hydrogen-rich and carbon-rich gas streams may be practiced using known separation equipment such as hydrogen membrane separator or a pressure swing adsorption unit, a cold box separation system or any combination of these. Using these techniques over 50% of the hydrogen present in the purge gas stream may be recovered.

The hydrogen-rich gas stream recovered from the purge gas stream desirably comprises >95% by volume of $H_2$. The separated hydrogen, in addition to being recycled to the methanol loop may also be used upstream in hydrodesulphurisation of the hydrocarbon feedstock and/or used to strip dissolved gases from the crude methanol. However, in a preferred embodiment, at least 90% by volume of the separated hydrogen-rich gas stream is fed to the methanol synthesis loop.

A portion of the carbon-rich gas stream, which will typically comprise carbon oxides and methane, is fed to the synthesis gas generation step in the reforming unit to form part of the make-up gas. However, preferably a portion of the carbon-rich gas stream is burned as fuel to control the build-up of inert gases. Where a membrane is used to separate the hydrogen-rich stream, the carbon-rich stream will be at a pressure that enables it to be sent for use as part of the hydrocarbon feedstock for reforming without further compression. Where a pressure swing absorption system is used to separate the hydrogen-rich stream, the carbon-rich stream will be at a low pressure, typically 2-5 bar abs, and so is less preferred in the present invention.

If desired, carbon dioxide may be removed from a portion of the carbon-rich stream in a CO2 removal unit. The CO2 removal unit may be any conventional CO2 removal unit that operates by physical absorption, chemical absorption, adsorption into a porous material, or uses a membrane to selectively separate CO2 from the carbon-rich stream, thereby forming a methane-rich stream. Whereas it may not be necessary to include the removal of carbon dioxide from the carbon-rich stream for natural gas feedstocks, for feedstocks heavier than natural gas, the removal of carbon dioxide from the carbon-rich stream is likely to be of benefit.

The purge gas stream mixture may contain methanol and so, if desired, upstream of the separation of the hydrogen-rich gas and the carbon-rich gas, methanol may be recovered from the purge gas stream using a water wash, and the recovered methanol and water sent for purification with the crude methanol.

The crude methanol stream recovered from the methanol production unit contains water, along with small amounts of higher alcohols and other impurities. The crude methanol may first be fed to a flash column where dissolved gases are released and separated from the crude liquid methanol stream. The crude liquid methanol may also be subjected to one or more purification stages including one or more, preferably two or three, stages of distillation in a methanol purification unit comprising one, two or more distillation columns. The de-gassing stage and distillation stages may be heated using heat recovered from the process, for example in the cooling of a product gas stream, or by other sources. Preferably at least a portion of the crude methanol is purified by distillation to produce a purified methanol product.

The purified methanol product may be subjected to further processing, for example to produce derivatives such as dimethyl ether or formaldehyde. Alternatively, the methanol may be used as a fuel.

The invention will be further described by reference to the figures in which;

FIG. 1 depicts a process according to one embodiment of the invention.

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

In FIG. 1, a natural gas stream 10 is mixed with a carbon-rich stream 12 and steam from line 14 and the resulting mixture fed via line 16 to a plurality of externally-heated, catalyst-filled tubes 18 of a heat exchange reformer 20. Whereas only three tubes are depicted there may be 10's or 100's of tubes. The hydrocarbons, carbon dioxide and steam react over the catalyst to form a primary reformed gas mixture comprising hydrogen, carbon dioxide, carbon monoxide, steam and unreacted methane. The primary reformed gas mixture is fed from the heat exchange reformer 20 via line 22 directly to an autothermal reformer 24 fed with an oxygen stream 26. In the autothermal reformer, the primary reformed gas mixture is partially combusted with the oxygen in a burner mounted near the top and the resulting hot, partially-combusted gas brought to equilibrium through a bed of steam reforming catalyst 28 disposed beneath the burner. The resulting secondary reformed synthesis gas stream is fed from the autothermal reformer 24 via line 30 directly to the shell side of the heat exchange reformer 20 where it heats the tubes 18 and is thereby partially cooled.

The partially cooled synthesis gas is fed from the heat exchange reformer 20 via line 32 to a heat recovery unit 34 comprising one or more heat exchangers, where it is further cooled to below the dew point to condense steam. Process condensate is removed from the cooled gas mixture using gas-liquid separation equipment in the heat recovery unit to produce a make-up gas. The make-up gas is recovered from the heat recovery unit via line 36, combined with a hydrogen-rich gas stream fed via line 38, compressed in a synthesis gas compressor 40 and fed from the compressor 40 via line 42 to a methanol synthesis unit 44.

The methanol synthesis unit comprises a methanol synthesis loop in which the compressed mixture of make-up gas and hydrogen-rich gas is mixed with a recycled stream of unreacted gas comprising hydrogen, carbon dioxide and carbon monoxide, and fed to one, two or more methanol synthesis reactors, each containing a methanol synthesis catalyst, operating in series or parallel to generate a product gas stream containing methanol. The product gas stream is cooled to condense and separate a liquid crude methanol from unreacted gas, a portion of which is compressed in a circulator and recycled to the first, second or further methanol synthesis reactor. The crude liquid methanol is recovered from the methanol synthesis unit 44 and fed via line 46 to a methanol purification unit 48 where it is subjected to de-gassing and one, two or three stages of distillation to produce a purified methanol product recovered from the purification unit 48 via line 50.

A portion of the unreacted gas is withdrawn from the methanol synthesis unit 44 upstream of the circulator and passed as a purge gas stream from the methanol synthesis unit 44 via line 52 to a hydrogen separation unit 54 in which the purge gas stream is separated into a hydrogen-rich stream and a carbon-rich stream by passing the purge gas stream through a membrane. The carbon-rich stream is recovered by line 56, a portion withdrawn via line 58 for use as a fuel gas, e.g. in a fired heater, and the remaining portion fed via line 12 to the hydrocarbon feed line 10. The hydrogen-rich gas stream is recovered from the separation unit 54 via line 38 and mixed with the make-up gas in line 36 to form an enriched feed gas. The enriched feed gas is fed to a suction or interstage of the synthesis gas compressor 40 to form a compressed enriched feed gas for the methanol synthesis unit 44.

The invention will be further described by reference to the following calculated examples prepared using conventional modelling software suitable for methanol processes. These examples all produce 5000 te/day of refined methanol product and in each case the oxygen flow has been calculated to satisfy the heat recovery balance around the heat exchange reformer.

EXAMPLE 1

Example 1 is an example in accordance with FIG. 1. The carbon-rich gas in the example is the retentate from a membrane separation unit that is fed with the purge gas from the methanol synthesis loop. 75% of the carbon-rich gas retentate is recycled as feedstock. The remaining 25% of the retentate is used as fuel for the fired heater, supplemented with natural gas.

EXAMPLE 2

Example 2 is the same as Example 1, but the $CO_2$ has been removed from the retentate recycle to demonstrate the impact of $CO_2$ removal.

COMPARATIVE EXAMPLE 3

Example 3 is a comparative example where none of the carbon-rich gas is recycled to the heat exchange reformer as feedstock.

|  | Example 1 | Example 2 | Comparative Example 3 |
| --- | --- | --- | --- |
| Recycle of carbon-rich gas | Yes | Yes | No |
| $CO_2$ removal from carbon-rich recycle | No | Yes | — |
| Natural gas flow relative to Example 1 | 100.0% | 100.0% | 101.8% |
| Oxygen flow to ATR relative to Example 1 | 100.0% | 100.1% | 100.3% |
| R-value of reformed gas | 2.005 | 2.024 | 2.034 |
| R-value of make-up gas (including hydrogen-rich recycle gas) | 2.062 | 2.130 | 2.158 |

The quantity of $CO_2$ in the carbon-rich recycle is relatively low (around 12 kmol/h for a 5000 te/day plant). As shown when comparing Example 1 and Example 2, it is not essential to include the removal of $CO_2$ from the carbon-rich recycle gas for the heat exchange reactor-based flowsheet used in the examples. However, for feedstocks heavier than the light natural gas used in the examples, the removal of $CO_2$ from the carbon-rich recycle is likely to be of benefit. Examples 1 and 2 have only 25% of the retentate uses as fuel, which is a 4-fold reduction in the fuel stream of Comparative Example 3. This 4-fold reduction in the fuel stream is readily achieved without excessive accumulation of inerts such as nitrogen and argon in the methanol synthesis loop. As the fuel value of the carbon-rich stream used as fuel is normally only in a small excess, a 4-fold reduction in the fuel stream demonstrates a benefit of the invention.

The invention claimed is:

1. A process for synthesising methanol comprising the steps of (i) forming a synthesis gas containing hydrogen, carbon monoxide and carbon dioxide from a hydrocarbon feedstock in a reforming unit comprising a heat exchange reformer and autothermal reformer in series; (ii) cooling the synthesis gas in the heat exchange reformer and one or more further stages of heat exchange, and recovering process condensate from the cooled synthesis gas to form a make-up gas; (iii) passing a feed gas comprising the make-up gas to a methanol synthesis loop comprising one or more methanol synthesis reactors; (iv) recovering a product gas mixture containing methanol from the methanol synthesis loop, cooling the product gas mixture to below the dew point to condense crude methanol, and separating the crude methanol from an unreacted gas mixture; and (v) recycling a portion of the unreacted gas mixture to the methanol synthesis loop and recovering a portion of the unreacted gas mixture as a purge gas stream, wherein a hydrogen-rich stream and a carbon-rich stream are separated from the purge gas, a portion of the hydrogen-rich stream is fed to the methanol synthesis loop and a portion of the carbon-rich stream is fed to the reformer unit.

2. The process according to claim 1 wherein the hydrocarbon feedstock is natural gas.

3. The process according to claim 2 wherein the steam for reforming the natural gas is provided using a saturator.

4. The process according to claim 1 wherein the heat exchange reformer comprises a steam reforming catalyst disposed in tubes that extend through a heat exchange zone formed between upper and lower tube sheets to which the synthesis gas is fed as heat exchange medium.

5. The process according to claim 1 wherein the autothermal reformer comprises a burner disposed near the top of the reformer to which a reformed gas from the heat exchange reformer and an oxygen-containing gas are fed, a combustion zone beneath the burner through which a flame extends, above a fixed bed of particulate steam reforming catalyst.

6. The process according to claim 5 wherein the oxygen-containing gas comprises >95% vol. $O_2$.

7. The process according to claim 1 wherein the composition of the make-up gas is 10-20 mol % carbon monoxide, 0.5-15 mol % carbon dioxide, 55-85% hydrogen and the balance one or more inert gases, including methane.

8. The process according to claim 7 wherein the R value of the make-up gas, before hydrogen-rich gas is added, is in the range 1.95-2.05, and after the hydrogen-rich gas is added, the R value is higher.

9. The process according to claim 1 wherein the make-up gas is compressed in a synthesis gas compressor to a desired loop pressure and the synthesis gas compressor is electrically driven.

10. The process according to claim 1 wherein the methanol synthesis loop comprises one, two or more methanol synthesis reactors each containing a bed of methanol synthesis catalyst, wherein the product gas mixture is recovered from at least one methanol synthesis reactor.

11. The process according to claim 10 wherein an unreacted gas mixture separated from a product gas mixture recovered from one methanol synthesis reactor is returned to the same or a different methanol synthesis reactor.

12. The process according to claim 10 wherein the unreacted gas is compressed by one or more circulating compressors and the circulating compressor is electrically driven.

13. The process according to claim 10 wherein the methanol synthesis reactors are cooled by a synthesis gas or by boiling water.

14. The process according to claim 10 wherein methanol synthesis is effected in the one or more methanol synthesis reactors at pressures in the range 10 to 120 bar abs, and at temperatures in the range 130° C. to 350° C.

15. The process according to claim 1 wherein the separation of the hydrogen-rich and carbon-rich streams is accomplished using a hydrogen membrane separator or a pressure swing adsorption unit, or a cold box separation system, or any combination of these.

16. The process according to claim 1 wherein the crude methanol is subjected to one or more steps of distillation to produce a purified methanol product.

\* \* \* \* \*